(12) United States Patent
Friedberg

(10) Patent No.: US 8,834,899 B2
(45) Date of Patent: Sep. 16, 2014

(54) PHOTODYNAMIC THERAPY-GENERATED MESOTHELIOMA VACCINE

(75) Inventor: Joseph Friedberg, Philadelphia, PA (US)

(73) Assignee: The Trustees of the University of Pennsylvania, Philadelphia, PA (US)

(*) Notice: Subject to any disclaimer, the term of this patent is extended or adjusted under 35 U.S.C. 154(b) by 1245 days.

(21) Appl. No.: 12/300,507

(22) PCT Filed: May 14, 2007

(86) PCT No.: PCT/US2007/011517
§ 371 (c)(1),
(2), (4) Date: Jan. 19, 2010

(87) PCT Pub. No.: WO2007/133728
PCT Pub. Date: Nov. 22, 2007

(65) Prior Publication Data
US 2010/0112011 A1 May 6, 2010

Related U.S. Application Data

(60) Provisional application No. 60/799,648, filed on May 12, 2006.

(51) Int. Cl.
*A61K 39/00* (2006.01)
*C12N 5/09* (2010.01)

(52) U.S. Cl.
USPC ........................................ 424/277.1; 435/375

(58) Field of Classification Search
None
See application file for complete search history.

(56) References Cited

U.S. PATENT DOCUMENTS

| 2002/0022032 | A1 | 2/2002 | Curry et al. | |
|---|---|---|---|---|
| 2003/0138881 | A1* | 7/2003 | Punnonen et al. | 435/69.1 |
| 2006/0104986 | A1* | 5/2006 | Duke et al. | 424/184.1 |
| 2006/0140858 | A1* | 6/2006 | Goldenberg et al. | 424/1.69 |
| 2006/0282132 | A1* | 12/2006 | Arai et al. | 607/88 |

FOREIGN PATENT DOCUMENTS

| WO | WO2004/112902 | * | 12/2004 |
|---|---|---|---|
| WO | WO2005/053743 | * | 6/2005 |

OTHER PUBLICATIONS

Mutti et al (Int Journal of Cancer, 1998, vol. 78, pp. 740-749).*
Aucouturier et al (Vaccine, Apr. 12, 2006 vol. 24, suppl. 2, pp. S44-S45).*
Wheeler (Salud p'ublica de M'exico, 1997, vol. 39, pp. 283-287).*
Efferson et al (Anticancer research, 2005, vol. 25, pp. 715-724).*
Bachman et al (Journal of Immunology, 2005, vol. 175, pp. 4677-4685).*
The Abstract of Shawler et al (Molecular Therapy, 2003, vol. 7, pp. S447-S448, Abstract No. 1161).*
Gollnick et al "Generation of effective antitumor vaccines using photodynamic therpay" Cancer Research, Vo. 62, No. 6, pp. 1604-1608, 2002.
Sterman et al "Aedvances in the Treatment of Malignant Pleural Mesotherlioma" Chest, vol. 116, No. 2 pp. 504-520, 1999.
Ait-Aissa SJ, Porcher C, Kretz-Remy G, et al. Induction of the hsp70 gene promotor by various anticancer drugs. Toxicol. In Vitro. 1999; 13:651-655.
Lanzavecchi A, Sallusto F. Regulation of T-cell immunity by dendritic cells. Cell. 2001; 106:263-266.
Dolmans, D. E. et al. Photodynamic therapy for cancer. Nat Rev Cancer, 3: 380-387, 2003.
Hopper, C. Photodynamic therapy: a clinical reality in the treatment of cancer. Lancet Oncol, 1: 212-219, 2000.
Hooper, C. Y. and Guymer, R. H. Review Article. New treatments in age-related macular degeneration. Clinical and Experimental Ophthalmology, 31: 376-391, 2003.
Jori, G. Tumour photosensitizers: approaches to enhance the selectivity and efficiency of photodynamic therapy. J Photochem Photobiol B, 36: 87-93, 1996.
Brown, S. B., Brown, E. A., and Walker, I. The present and future role of photodynamic therapy in cancer treatment. Lancet Oncol, 5: 497-508, 2004.
Vrouenraets, M. B., Visser, G. W., Snow, G. B., and van Dongen, G. A. Basic principles, applications in oncology and improved selectivity of photodynamic therapy. Anticancer Res, 23: 505-522, 2003.
Mulrooney, C. A., Li, X., DiVirgilio, E. S., and Kozlowski, M. C. General approach for the synthesis of chiral perylenequinones via catalytic enantioselective oxidative biaryl coupling. J Am Chem Soc, 125: 6856-6857, 2003.
Friedberg, J. S., Mick, R., Stevenson, J. P., Zhu, T., Busch, T. M., Shin, D., Smith, D., Culligan, M., Dimofte, A., Glatstein, E., and Hahn, S. M. Phase II trial of pleural photodynamic therapy and surgery for patients with non-small-cell lung cancer with pleural spread. J Clin Oncol, 22: 2192-2201, 2004.
Dougherty, T. J., Gomer, C. J., Henderson, B. W., Jori, G., Kessel, D., Korbelik, M., Moan, J., and Peng, Q. Photodynamic therapy. J Natl Cancer Inst, 90: 889-905, 1998.
Korbelik, M. and Dougherty, G. J. Photodynamic therapy-mediated immune response against subcutaneous mouse tumors. Cancer Res, 59: 1941-1946, 1999.
O'Mahony, D., Kummar, S., and Gutierrez, M. E. Non-Small-Cell Lung Cancer Vaccine Therapy: A Concise Review. J Clin Oncol, 23, 2005.
Merritt, R. E., Yamada, R. E., Wasif, N., Crystal, R. G., and Korst, R. J. Effect of inhibition of multiple steps of angiogenesis in syngeneic murine pleural mesothelioma. Ann Thorac Surg, 78: 1042-1051, 2004.
Nestle, F. O., Tonel, G., and Farkas, A. Cancer vaccines: the next generation of tools to monitor the anticancer immune response. PLoS Med, 2: e339, 2005.

(Continued)

*Primary Examiner* — Karen Canella
(74) *Attorney, Agent, or Firm* — Mark S. Cohen; Pearl Cohen Zedek Latzer Baratz LLP

(57) ABSTRACT

This invention relates to a vaccine for mesothelioma generated using photodynamic therapy and its use in methods and compositions for treating mesothelioma.

31 Claims, 4 Drawing Sheets

(56) References Cited

OTHER PUBLICATIONS

Stevenson, F. K. Update on cancer vaccines. Curr Opin Oncol, 17: 573-577, 2005.

Hockertz, S. Present and Future of Cancer Vaccines. Toxicology, 214: 151-161, 2005.

Chang, M.-H., Chen, C.-J., Lai, M.-S., Hsu, H.-M., Wu, T.-C., Kong, M.-S., Liang, D.-C., Shau, W.-Y., Chen, D.-S., and The Taiwan Childhood Hepatoma Study Group Universal Hepatitis B Vaccination in Taiwan and the Incidence of Hepatocellular Carcinoma in Children. N Engl J Med, 336: 1855-1859, 1997.

Koutsky, L. A., Ault, K. A., Wheeler, C. M., Brown, D. R., Barr, E., Alvarez, F. B., Chiacchierini, L. M., Jansen, K. U., and the Proof of Principle Study Investigators A Controlled Trial of a Human Papillomavirus Type 16 Vaccine. N Engl J Med, 347: 1645-1651, 2002.

Merck Newsroom. Merck's investigational vaccine Gardasil(tm) prevented 100 per cent of cervical pre-cancers and non-invasive cervical cancers associated with HPV types 16 and 18 in new clinical study. Press release Oct. 6, 2005. www.merck.com/newsroom/press_releases/research_and_development/2005_1006.html.

Nemunaitis, J. GVAX (GMCSF gene modified tumor vaccine) in advanced stage non small cell lung cancer. J Control Release, 91: 225-231, 2003.

Berd, D., Sato, T., Maguire, H. C., Jr., Kairys, J., and Mastrangelo, M. J. Immunopharmacologic analysis of an autologous, hapten-modified human melanoma vaccine. J Clin Oncol, 22: 403-415, 2004.

Vlad, A. M., Kettel, J. C., Alajez, N. M., Carlos, C. A., and Finn, O. J. MUC1 immunobiology: from discovery to clinical applications. Adv Immunol, 82: 249-293, 2004.

Pass HI, Temeck BK, Kranda K, et al. Phase III randomized trial of surgery with or without intraoperative photodynamic therapy and postoperative immunochemotherapy for malignant pleural mesothelioma. Annals of Surgical Oncology. 1997; 4(8):628-33.

Antman KH, Pass HI, Schiff PB. Benign and malignant mesothelioma (Chap). In DeVita VT, Hellman S, Rosenberg SA, eds. Cancer, Principles and Practice of Oncology. Philadelphia: Lippincott-Raven, 1997. pp. 1853-1878.

Sugarbaker DJ, Flores RM, Jaklitsch MT, et al. Resection margins, extrapleural nodal status, and cell type determine postoperative long-term survival in trimodality therapy of malignant pleural mesothelioma: results in 183 patients. Journal of Thoracic & Cardiovascular Surgery. 1999; 117(1):54-63; discussion 63-5.

Pass HI, Kranda K, Temeck BK, et al. Surgically debulked malignant pleural mesothelioma: results and prognostic factors. Annals of Surgical Oncology. 1997; 4(3):215-22.

Takeuchi Y, Kurohane K, Nango M, Oku N. Intensive tumor suppression by anti-angiogenic photodynamic therapy with polycation-modified liposomal photosensitizer. Cellular & Molecular Biology Letters. 2002; 7(2):301.

Cecic I, Parkins CS, Korbelik M. Induction of systemic neutrophil response in mice by photodynamic therapy of solid tumors. Photochemistry & Photobiology. 2001; 74(5):712-20.

Banchereau, J., Schuler-Thurner, B., et al. Dendritic cells as vectors for therapy. Cell, 106: 271-274, 2001.

Liu B, DeFilippo AM, Li Z. Overcoming Immune Tolerance to Cancer by Heat Shock Protein Vaccines. Molecular Cancer Therapeutics. 2001; 1:1147-51.

Morimoto RI, Santoro MG. Stress-inducible response and heat shock proteins: new pharmacologic targets for cytoprotection. Nat. Biotechnol. 1998; 16:833-838.

Srivastava PK, Menoret A, Basu RJ, et al. Heat shock proteins come of age: primitive functions acquire new roles in an adaptive world. Immunity. 1998; 8:657-665.

Srivastava, PK, Amato RJ. Heat shock proteins: the 'Swiss Army Knife' vaccines against cancers and infectious agents. Vaccine. 2001; 19:2590-97.

Gomer CJ, Ryter SW, Ferrario A, et al. Photodynamic therapy-mediated oxidative stress can induce expression of heat shock proteins. Cancer Res. 1996; 56:2355-60.

Luna MC, Ferrario A, Wong S, Fisher AM, Gomer CJ. Photodynamic therapy-mediated oxidative stress as a molecular switch for the temporal expression of genes ligated to the human heat shock promotr. Cancer Res. 2000; 60:1637-44.

Wysocka A, Krawcyzk Z. Green fluorescent protein as a marker for monitoring activity of stress-inducible hsp70 rat gene promotor. Mol. Cell Biochem. 2000; 215:153-156.

Sinkovics JG, Horvath JC. Vaccination against human cancers (Review). Int. J. Oncol. 2000; 16:81-96.

Bodey B, Bodey B Jr, Siegel SE, Kaiser HE. Failure of cancer vaccines: the significant limitations of their approach to immunotherapy. Anticancer Res. 2000; 20:2665-76.

Yom S, Busch TM, Friedberg JS, Wileyto E, et al. Elevated serum cytokine levels in mesothelioma patients who have undergone pleurectomy or extrapleural pneumonectomy and adjuvant intraoperative photodynamic therapy. Photochemistry and Photobiology. 2003; 78(1):75-81.

\* cited by examiner

PHOTODYNAMIC THERAPY-GENERATED MESOTHELIOMA VACCINE

CROSS-REFERENCE TO RELATED APPLICATIONS

This application is a National Phase Application of PCT International Application No. PCT/US07/11517, International Filing Date 12 May 2007, claiming priority of U.S. Provisional Patent Application 60/799,648, filed 12 May, 2006, both which are incorporated herein by reference in their entirety.

FIELD OF INVENTION

This invention is directed to a vaccine for mesothelioma generated using photodynamic therapy and its use in methods and compositions for treating mesothelioma.

BACKGROUND OF THE INVENTION

Malignant mesothelioma is a cancer that most commonly afflicts the pleura. The parietal and visceral pleura are layers of tissue that invest the lung and are lined by a single layer of mesothelial cells. The parietal pleura lines the chest wall and the diaphragm, is of a consistent thickness, and receives its blood supply from the intercostal arteries. The visceral pleura covers the lungs, has a varying thickness, and is supplied by blood from the bronchial circulation that drains into the pulmonary veins. This cancer arises from the mesothelial cells that line both the visceral and parietal pleura. The tumor may present as either a localized and discrete tumor or as a diffuse growth.

Caused primarily by occupational asbestos exposure, malignant mesothelioma is especially difficult to treat; patients tend not to respond to single-modality therapies, such as radiotherapy, chemotherapy, or surgery and have an expected survival of only 4 to 12 months. More than 2000 cases per year are diagnosed in the United States alone, with expected increases in frequency through 2020. Mesothelioma is not associated with cigarette smoking, but other possible progenitors besides asbestos contact, such as simian virus 40 are still being considered. Because of both a lack of adequate treatment options and the increasing incidence in both the U.S. and abroad, development of improved treatments for this disease is a necessary goal.

Cancer cell vaccines are intact, dead cells produced by treating cancer cells of a patient or animal with physical or chemical methods, such that after treatment, those cells will possess therapeutic or auxiliary therapeutic effect. The methods used to treat the cancer cells include radiation, or treating with organic solvent, etc. After introduction of the vaccine to the patient using injection, or other method, the cancer cell vaccine can stimulate or enhance the patient's immune response against the targeted cancer. Genetically-modified vaccine, polypeptide cancer vaccine, and gene/DNA vaccines are all vaccines having therapeutic effect on the targeted cancer, and made by using the cancer antigen or its fragments, or polynucleotides coding for such cancer antigen or its fragments, and carriers/cells containing the polynucleotides.

Cancer vaccine studies have become an important area in the fight to cure cancer and save the lives of patients worldwide. It has been recognized in the medical research and clinical studies that one of the key factor for the success of any cancer therapy is its ability to distinguish neoplastic cells, which should be killed by the chosen therapy, from normal cells, which should be unaffected, and left alone as much as possible, by the therapy.

SUMMARY OF THE INVENTION

In one embodiment, the invention provides a method of preparing a vaccine for the treatment of malignant mesothelioma comprising the steps of: treating mesothelioma cells with a photosensitizer; removing the photosensitizer from the cells; incubating the photosensitized cells; and exposing the photosensitized cells to electromagnetic energy source; whereby the exposure of the photosensitized incubated cells to the electromagnetic radiation kills the cells, thereby resulting in non-viable cells capable of inducing immunological response.

In another embodiment, the invention provides a vaccine for the treatment of mesothelioma prepared by treating mesothelioma cells with a photosensitizer; removing the photosensitizer from the cells; incubating the photosensitized cells; and exposing the photosensitized cells to electromagnetic energy source; whereby the exposure of the photosensitized incubated cells to the electromagnetic radiation kills the cells, thereby resulting in non-viable cells capable of inducing immunological response.

In one embodiment, the invention provides a composition for treating, preventing or ameliorating mesothelioma in a subject, comprising: a pharmaceutically acceptable carrier and an immunologically effective amount of a vaccine for the treatment of mesothelioma prepared by treating mesothelioma cells with a photosensitizer; removing the photosensitizer from the cells; incubating the photosensitized cells; and exposing the photosensitized cells to electromagnetic energy source; whereby the exposure of the photosensitized incubated cells to the electromagnetic radiation kills the cells, thereby resulting in non-viable cells capable of inducing immunological response.

In another embodiment, the invention provides a method of treating mesothelioma in a subject, comprising the step of administering to said subject a composition comprising a vaccine for the treatment of mesothelioma prepared by treating mesothelioma cells with a photosensitizer; removing the photosensitizer from the cells; incubating the photosensitized cells; and exposing the photosensitized cells to electromagnetic energy source; whereby the exposure of the photosensitized incubated cells to the electromagnetic radiation kills the cells, thereby resulting in non-viable cells capable of inducing immunological response.

In one embodiment, the invention provides a method of treating mesothelioma in a subject, comprising administering to said subject a composition for treating, preventing or ameliorating mesothelioma in a subject, comprising: a pharmaceutically acceptable carrier and an immunologically effective amount of a vaccine for the treatment of mesothelioma prepared by treating mesothelioma cells with a photosensitizer; removing the photosensitizer from the cells; incubating the photosensitized cells; and exposing the photosensitized cells to electromagnetic energy source; whereby the exposure of the photosensitized incubated cells to the electromagnetic radiation kills the cells, thereby resulting in non-viable cells capable of inducing immunological response.

In another embodiment, the invention provides a combination vaccine, comprising a vaccine for the treatment of mesothelioma prepared by treating mesothelioma cells with a photosensitizer; removing the photosensitizer from the cells; incubating the photosensitized cells; and exposing the photosensitized cells to electromagnetic energy source; whereby the exposure of the photosensitized incubated cells to the electromagnetic radiation kills the cells, thereby resulting in non-viable cells capable of inducing immunological response, together with one or more antigens that trigger an immune response that protects a subject against mesothelioma, and a pharmaceutically acceptable carrier.

In one embodiment, the invention provides a method of increasing antigenicity of a tumor cell, comprising the steps of treating the tumor cell with a photosensitizer; removing the photosensitizer from the cells; incubating the photosensitized cells; and contacting the photosensitized cells with electromagnetic energy source; whereby the exposure of the photosensitized incubated cells to the electromagnetic radiation evokes IFN-γ secretion, induces increased expression of HSP-70, or their combination thereby increasing the antigenicity of the tumor cell.

BRIEF DESCRIPTION OF THE DRAWINGS

The invention will be better understood from a reading of the following detailed description taken in conjunction with the drawings in which like reference designators are used to designate like elements, and in which.

DETAILED DESCRIPTION OF THE INVENTION

Figure 1:
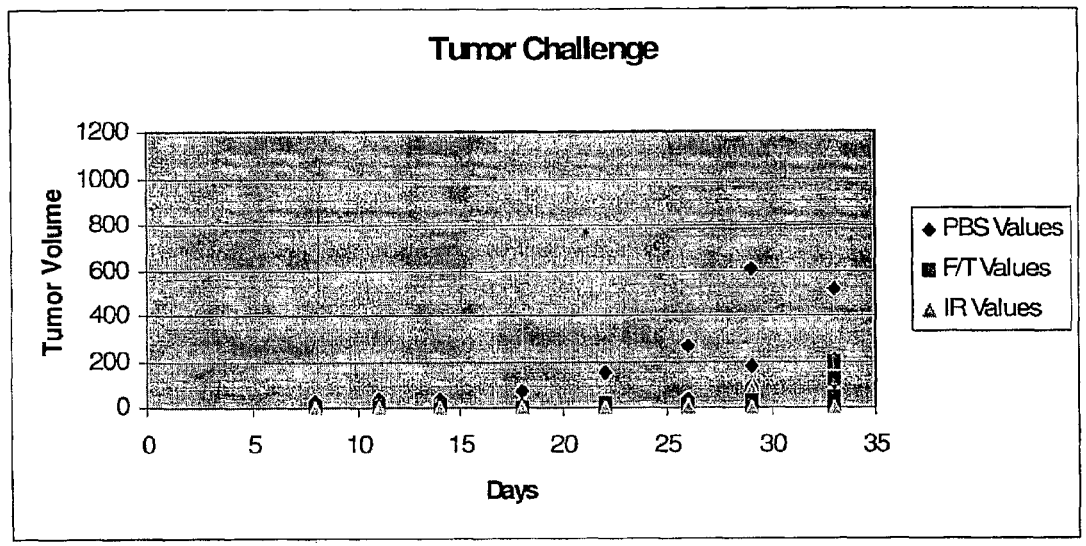
FIG. 1 shows scatter plot of tumor volumes for three treatment groups: control (PBS), F/T, and IR

This invention relates in one embodiment to a vaccine for mesothelioma generated using photodynamic therapy and its use in methods and compositions for treating mesothelioma.

Photodynamic therapy (PDT) is a technique used for killing cancer cells that involves cell exposure to a photoreactive drug or photosensitizer in the presence of oxygen and light. PDT has proven effective in the treatment of other pathologies, ranging from esophageal and gastrointestinal tumors to macular degeneration. Upon exposure to light with a wavelength specific to the photosensitizer, the sensitizer is transformed from its ground state (a singlet state) into an electronically excited triplet state. From the excited state, it may undergo two different mechanisms, either a type I or type II reaction. In a type I reaction, the excited triplet oxygen can form radicals through electron transfer by reacting directly with a substrate, such as the cell membrane. These radicals can then react with other molecules and produce oxygenated products. In a type II reaction, the radical reacts with oxygen immediately and produces a singlet oxygen, which is extremely reactive. The end result of both of these mechanisms is the eventual creation of a cytotoxic oxygen species and cell death. Many porphyrin-type photosensitizers react in one embodiment with the cell membrane, or mitochondria, the rough endoplasmic reticulum, and lysosomes have also been cited as primary targets in other embodiments.

In one embodiment, the generation of B-cells, produce antibodies having reactivity specific for tumor cell antigens, such as cell surface antigens in another embodiment. In one embodiment, the vaccines described herein elicit an anti-cancer immune response in a subject, through the administration of a composition comprising antigen presenting cells, which are capable of inducing T cell activation, wherein the antigen presenting cells are cancer cells, which are derived in one embodiment, from the subject or are the same cancer cell type as the patient-derived cancer cells, and wherein the cancer is mesothelioma.

Therefore, according to this aspect of the invention and in one embodiment, the invention provides a method of preparing a vaccine for the treatment of malignant mesothelioma comprising the steps of: treating mesothelioma cells with a photosensitizer; removing the photosensitizer from the cells; incubating the photosensitized cells; and exposing the photosensitized cells to electromagnetic energy source; whereby the exposure of the photosensitized incubated cells to the electromagnetic radiation kills the cells, thereby resulting in non-viable cells capable of inducing immunological response.

In another embodiment, the term "vaccine" as used herein includes a therapeutic or immunotherapeutic vaccine. In another embodiment, the vaccine is used in a host already diagnosed with cancer and can be administered to stimulate an immune response against a poorly immunogenic tumor. The immune response can lead to reduced tumor growth and spread, elimination of tumor cells by cellular and humoral immune responses, and/or prevention or delay of tumor recurrence upon partial or complete remission of the cancer, which in one embodiment is mesothelioma, or malignant mesothelioma.

In one embodiment, the term "photodynamic therapy" refers to a process whereby light of a specific wavelength is directed to tissues or cells undergoing treatment or investigation that have been rendered photosensitive through the administration of a photoreactive or photosensitizing agent. The objective may be either diagnostic in one embodiment, where the wavelength of light is selected to cause the photoreactive agent to fluoresce, thus yielding information about the tissue without damaging the tissue, or therapeutic, where the wavelength of light delivered to the target tissue under treatment causes the photoreactive agent to undergo a photochemical interaction with oxygen in the tissue under treatment that yields high energy species, such as singlet oxygen, causing local tissue lysing or destruction, or the triggering of immunoresponse of the photosensitized tissue or cell The method of van Lier (Photobiological Techniques 216: 85-98 (Valenzo et al., eds. 1991)) can be used to confirm the ability of any given composition to generate singlet oxygen effectively, thus making it a good candidate for use in photodynamic therapy for creation of the vaccines used in the compositions and methods described herein.

In one embodiment. the term "photosensitizer" or "photosensitizing agent" refers to a chemical compound that upon exposure to photoactivating light is activated, converting the photosensitizing agent itself, or some other species, into a cytotoxic form, whereby target cells are killed or their proliferative potential diminished. Thus, photosensitizing agents may exert their effects by a variety of mechanisms, directly or indirectly. In one embodiment, certain photosensitizing agents become directly toxic when activated by light, whereas others act to generate toxic species, e.g. oxidizing agents such as singlet oxygen or oxygen-derived free radicals, which are extremely destructive to cellular material and biomolecules such as lipids, proteins and nucleic acids in other embodiments. In another embodiment, psoralens are directly acting photosensitizers; which upon exposure to light form adducts and cross-links between the two strands of DNA molecules, thereby inhibiting DNA synthesis. Virtually any chemical compound that, upon exposure to photoactivating light, is converted into or gives rise to a cytotoxic form may be used in this invention. Generally, the chemical compound is nontoxic to the animal or in the cell to which it is administered or is capable of being formulated in a nontoxic composition, and the chemical compound in its photodegraded form is also nontoxic. A listing of representative photosensitive chemicals may be found in Kreimer-Bimbaurn, Sem. Hematol. 26:157-73, 1989.

Photosensitive compounds include in one embodiment, chlorins, bacteriochlorins, phthalocyanines, porphyrins, purpurinimides, pheophorbides, pyropheophorbides, merocyanines, psoralens, benzoporphyrin derivatives (BPD), talaporfin sodium and porfimer sodium and pro-drugs such as deltaminolevulinic acid, which can produce drugs such as protoporphyrin. Other compounds include indocyanine green; methylene blue; toluidine blue; texaphyrins; and any other agent that absorbs light in a range of 400 nm-1200 nm.

In one embodiment, the photosensitizer used in the methods of preparing the vaccine used in the embodiments of vaccines, compositions and methods described herein, is hematoporphyrin derivative (HPD). In another embodiment, the photosensitizer is a benzoporphyrin derivative (BPD). In another embodiment, the photosensitizer is a tetra(m-hydroxyphenyl)chlorin (foscan). In another embodiment, the photosensitizer is a mono-L-aspartylchlorin e6, lutetium texaphyrin. In another embodiment, the photosensitizer is a zinc phthalocyanine, or in another embodiment, the photosensitizer is a combination thereof.

In one embodiment, the mesothelioma cells used for generating the vaccines used in the vaccines, compositions and methods described herein are generated from exponentially growing tumor cells. Exponential growth, refers in one embodiment to the simplest possible growth, which is cellular division with a constant dividing time.

Malignant mesothelioma refers in one embodiment, to a cancer that affects the pleura. The parietal and visceral pleura are layers of tissue that invest the lung and are lined by a single layer of mesothelial cells. The parietal pleura lines the chest wall and the diaphragm, is of a consistent thickness, and receives its blood supply from the intercostal arteries. The visceral pleura covers the lungs, has a varying thickness, and is supplied by blood from the bronchial circulation that drains into the pulmonary veins. This cancer arises from the mesothelial cells that line both the visceral and parietal pleura. The tumor may present as either a localized and discrete tumor or as a diffuse growth.

In one embodiment, the method of preparing the vaccine used in the vaccines, compositions and methods described herein is generated by treating exponentially growing mesothelioma cells with a photosensitizer; removing the photosensitizer from the cells; incubating the photosensitized cells; and exposing the photosensitized cells to electromagnetic energy source; whereby the exposure of the photosensitized incubated cells to the electromagnetic radiation kills the cells; thereby resulting in non-viable cells capable of inducing immunological response, wherein the step of treating the exponentially growing mesothelioma cells with the photosensitizer is followed in one embodiment by incubation of the photosensitizer-treated cells for between about 1 to about 48 hours, or in another embodiment, between about 3 to about 36 hours, or in another embodiment, between about 3 to about 24 hours, or in another embodiment, between about 6 to about 24 hours, or in another embodiment, between about 8 to about 12 hours.

In another embodiment, the mesothelioma cells used for the vaccines, compositions and methods described herein, are exponentially growing malignant mesothelioma cells that do not produce TGF-β. Transforming growth factor (TGF)-β is a $M_r$ 25,000 homodimeric protein with multiple mammalian forms, which function as a tumor suppressors in one embodiment, or tumor enhancers in other embodiments. In one embodiment, loss of TGF-β (as seen in hemizygous Tgfb-1-null mice) or loss of function of the TGF-β receptors (especially TGF-β type II receptor) clearly enhances tumorigenicity.

In one embodiment, photochemical internalization (PCI) of certain photosensitizing substances (photosensitizers) are used to improve the ability of killing the tumor cells used in the vaccines, compositions and methods described herein. Photosensitizers include members of the following classes of compounds: porphyrins, chlorins, bacteriochlorins, purpurins, phthalocyanines, naphthalocyanines, texaphyrins, and non-tetrapyrrole photosensitizers. Specific examples include Photofrin, benzoporphyrin derivative, tin etiopurpurin, sulfonated chloroaluminum phthalocyanine and methylene blue. The photosensitizer can be targeted, in one embodiment, mesothelial cells, by conjugation to a targeting moiety such as a protein, peptide, or microparticle that can specifically react with the surface of the mesothelial cells. For systemic administration, dosage is between about 0.1 mg/kg and about 50 mg/kg. in another embodiment, the dosage level is between about 0.5 mg/kg and about 10 mg/kg. In other embodiments of the invention, the administration of the photosensitizer is local. Local administration can be intratumoral, or systemic. In one embodiment, the photosensitizer used to generate the vaccines used in the vaccines, compositions and methods described herein, the photosensitizer is present at a dose of between about 10 to about 50 µg/mL, or in another embodiment, between about 20 to about 40 µg/mL, or in another embodiment, between about 20 to about 30 µg/mL, or in another embodiment, between about 22 to about 28 µg/mL, or in another embodiment, between about 24 to about 26 µg/mL, or in another embodiment, about 25 µg/ml.

In one embodiment, the step of exposing the incubated, photosensitized cells to electromagnetic energy source in the methods of preparing the vaccines and compositions used in the methods described herein, is preceded by placing the photosensitized cells in serum-free media and transferring them to a plate in preparation for exposure.

In one embodiment, the electromagnetic energy source used, is a laser light source. Although lasers are used in one embodiment for the delivery of phototherapeutic light, any high energy light source is useful for the methods described herein. Suitable high energy light sources can also include xenon light, halogen light, arc light sources. In one embodiment, lasers provide the form of optical radiation to activate photosensitizers.

In one embodiment, lasers produce high energy monochromatic light of a specific wavelength with a narrow bandwidth for a specific photosensitizer. The laser light can be focused in one embodiment, or passed down an optical fiber and directly delivered to the target site through a specially designed illuminator tip, in another embodiment a microlens or a cylindrical or spherical diffuser. Argon dye, potassium-titanyl-phosphate (KTP) dye, metal vapor lasers, and most recently diode lasers have been used for clinical PDT around the world. In one embodiment, KTP-dye modular combination system (Laserscope PDT Dye Module) is used. In another embodiment a portable, light-weight, and less expensive diode lasers (e.g., DIOMED 630 PDT; Diomed Inc.) is used to generate the vaccines described in the embodiments herein. In one embodiment, the diode laser is engineered into a multi-channel unit to meet a highly specialized PDT procedure, which may require multi-channel diode lasers and each independent light output channel to simultaneously provide the light sources of variable power (e.g., Ceralas PDT 762 nm; CeramOptec GmbH of Biolitec AG). In another embodiment, the multichannel laser is used when a combination of photosensitizers are used to generate the vaccines used in the compositions and methods described herein, creating a vaccine which is effective agains more than a single tumor.

In one embodiment, the lasers used in the methods described herein generate light at a wavelength of between about 400 to about 1200 nm, or in another embodiment, between about 450 to about 1000 nm, or in another embodiment, between about 500 to about 800 nm, or in another embodiment, between about 550 to about 750 nm, or in another embodiment, between about 600 to about 700 nm, or in another embodiment, between about 620 to about 680 nm, or in another embodiment, between about 625 to about 635 nm.

In one embodiment, the electromagnetic (EM) energy dosage used to generate the vaccines used in the combination vaccines, compositions and methods described herein, is above about 2.5 j/cm$^2$. In one embodiment, the energy dosage refers to the radiant energy arriving at a surface per unit area, expressed in another embodiment as joules or millijoules per square centimeter. In another embodiment, the electromagnetic energy dosage refers to the terms "radiant exposure," "light dose," and "total effective dosage". In one embodiment, the EM energy dosage, refers to the time-integral of irradiance.

In one embodiment, the methods of preparing the vaccine for treating mesotheliomas described in the embodiments hereinabove, generate the vaccines described herein, which are used in the compositions and methods described herein.

According to this aspect of the invention and in one embodiment, provided herein is an immunotherapeutic vaccine for the treatment of mesothelioma prepared by treating mesothelioma cells with a photosensitizer; removing the photosensitizer from the cells; incubating the photosensitized cells; and exposing the photosensitized cells to electromagnetic energy source; whereby the exposure of the photosensitized incubated cells to the electromagnetic radiation kills the cells, thereby resulting in non-viable cells capable of inducing immunological response.

In one embodiment, the vaccine described herein will stimulate production of antibodies against normally tolerated tumor and other relevant antigens in human cancer patients. In another embodiment, immunotherapy has been considered potentially useful for mesothelioma because mesothelioma has shown certain immunological traits, such as spontaneous regression, the fact that neither human nor murine cell lines constitutively express class II MHC, MM cell lines, like most other tumours, do not generally express the co-stimulatory molecules B7-1 or B7-2 and are relatively devoid of membrane adhesion molecules, such as ICAM-1, although they do express vascular cell adhesion molecule-1 (VCAM-1) on their membrane.

To elicit anti-tumor immune response, various cell types have been employed as cellular adjuvants with tumor antigens, and in certain embodiments, dendritic cells (DC), cultured with tumor cell lysates, synthetic tumor antigens, or peptides purified from tumor cells, induce significant anti-tumor immunity in vivo. In one embodiment, various cell types and co-factors are administered in combination with the vaccines described herein. In another embodiment. dendritic cells (DC), cultured with tumor cell that were treated according the methods of generating vaccines described herein, are used in the compositions and methods described herein.

In one embodiment, the vaccine described herein, used in the compositions and methods herein are used in combination with another immunostimulating molecule. In another embodiment, the term "immunostimulating molecule" refers to cytokines, hematopoietic growth factors, and mesothelioma immunogens. The term "cytokine" refers to bioactive molecules derived from cells and capable of affecting cells' behavior, e.g., growth, migration, killing capacity, differentiation, secretion, etc. The term "lymphokine" means essentially same as the cytokine but usually refers to bioactive molecules derived from lymphocytes and affecting predominantly the behavior of lymphocytes.

The term "immunotherapeutic vaccine," as opposed to the notion of a "prophylactic vaccine," means in another embodiment, a vaccine administered to treat and/or prevent further progression of the disease in a host already diagnosed with the disease. The term "administering" means any method of providing a host in need thereof with a vaccine, including oral, intranasal, topical, transdermal, parenteral, e.g., intravenous, subcutaneous, intradermal, intramuscular, intratumoral, intraperitoneal and other means of delivery known in the art.

In another embodiment, a major advantage is observed for subjects vaccinated with PDT lysates rather than IR or F/T. In one embodiment, PDT-generated lysates evoke greater IFN-γ secretion and induce increased expression of HSP-70 thereby increasing the antigenicity of the tumor cell. In one embodiment, Heat shock proteins (HSP) refer to highly conserved, abundantly expressed proteins functioning in certain embodiments as intracellular molecular chaperones of nascent proteins (during their synthesis, folding, transport, assembly, and stabilization), and of degradation of naïve, aberrantly folded, damaged, or mutated proteins. In another embodiment, HSP's participate in signal transduction pathways and regulate inflammatory and immune response. In one embodiment, a substantial increase in the synthesis of HSPs is induced by a wide variety of stimuli including in one embodiment, physiologic (cell growth and differentiation and tissue development), or pathologic (infections, inflammation, malignancy, or autoimmunity), or environmental stress (heat shock, heavy metals, and oxygen radicals) in other embodiments.

In one embodiment, a substantial majority of human tumors (head-and-neck cancers) are positive for membrane-expressed HSP-70, whereas in another embodiment, normal tissues is not. In another embodiment, chemotherapy, radiotherapy, and hyperthermia induce or increase surface HSP-70 expression on treated cancer cell. In another embodiment, the basic insult inflicted by PDT is a form of oxidative stress, thereby inducing the expression of various HSPs and this response is at the level of transcription, including in one embodiment, the expression of HSP-70. In another embodiment, HSP-70 released from PDT-treated tumor cells is captured by macrophages triggering in another embodiment, in these cells—Toll-like receptor (TLR)—based signal transduction activity, resulting in the production of inflammatory cytokine tumor necrosis factor α (TNF-α).

In one embodiment, vaccination with PDT-generated tumor cell lysates elicits a tumor-specific immune response demonstrated in one embodiment, by protection against subsequent tumor inoculation, induction of tumoricidal activity in the spleen, and increased numbers of IFN-γ-secreting splenic cells. In another embodiment, UV or IR used as the electromagnetic energy source in producing the vaccines described herein, are not as effective as PDT vaccines at activating tumor-specific IFN-γ-secreting cells and at increasing splenic cytolytic activity. In one embodiment, PDT administered to malignant cells aide in the tumor identification and ultimate destruction by the host immune system.

In one embodiment, the term "treatment" refers to any manner in which one or more of the symptoms of a disease or disorder are ameliorated or otherwise beneficially altered. Treatment also encompasses any pharmaceutical use of the vaccines herein, such as use for treating hyperproliferating tissue or neovascularization mediated diseases or disorders, or diseases or disorders in which hyperproliferating tissue or neovascularization is related to mesothelioma.

Subjects may be vaccinated at any time, including just prior to or at the time of eating. Supplemental administrations, or boosters, may be required in another embodiment, for full protection. One method of detecting whether adequate immune protection is to determine tumor growth and related symptoms in the subject after vaccination. Thus, the vaccine described herein may be administered at any time during the life of a particular subject to be vaccinated, depending upon several factors, including, for example, the timing of diagnosis of mesothelioma in the subject, etc. Effective vaccination may require only a primary vaccination, or a primary vaccination with one or more booster vaccinations. Booster vaccinations may be administered at any time after primary vaccination depending, for example, on the immune response after primary vaccination, the stage of mesothelioma, observed side effects, the health of the subject, etc. The timing of vaccination and the number of boosters, if any, will preferably be determined by a physician based on analysis of all relevant factors, some of which are described above for certain embodiments.

In one embodiment, the vaccines described hereinabove, generated by the methods described hereinabove are used in the compositions and the methods described herein.

In one embodiment, described herein is a composition for treating, preventing or ameliorating mesothelioma in a subject, comprising: a pharmaceutically acceptable carrier and an immunologically effective amount of a vaccine for the treatment of mesothelioma prepared by treating mesothelioma cells with a photosensitizer; removing the photosensitizer from the cells; incubating the photosensitized cells; and exposing the photosensitized cells to electromagnetic energy source; whereby the exposure of the photosensitized incubated cells to the electromagnetic radiation kills the cells, thereby resulting in non-viable cells capable of inducing immunological response.

In another embodiment, the compositions described herein further comprise an adjuvant, cytokines, or their combination. In one embodiment, the adjuvant is an oil-in-water emulsion.

In one embodiment, the compositions described herein comprisise a cancer vaccine based on the weak immunogenicity of target tumor antigen mixed with adjuvant in order to produce, recover or enhance anti-cancer immune response and kill the residual or invasive tumor cells. The potential target of anti-self-antigen or anti-tumor includes in other embodiments, over expressed protein, tissue-specific differentiation antigen, development protein which tumor cells abnormally expressed, and the like.

The compositions described herein comprise in one embodiment the use of various drug delivery systems or formulations. These could further improve the adjuvant property or a depot of the vaccine described above. The vaccines could be formulated in a form of a liquid solution, a powder, a polymer system, a biopolymer and natural polymer, a microparticle, a bioadhesive polymer, needleless delivery system, a scarification delivery system, or a tyne delivery system or formulated with any known or later developed drug delivery systems in other embodiments.

In one embodiment, the vaccines, or mesothelioma tumor cells killed using PDT used in the vaccines and prepared according to the methods of the invention, as are described herein, are a combination vaccine, together with one or more antigens that trigger an immune response that protects a subject against a disease or an associated pathological condition, and a pharmaceutically acceptable carrier. In one embodiment, theses antigens are one or more antigens that trigger an immune response that protects a subject against a disease or a pathological condition is SV40, or IL-2, IL12, $CD40^+$ or their combination in another embodiment.

In one embodiment, the compositions described herein, is in a lyophilized form. In another embodiment, the compositions, vaccines used in the methods described herein, are in the form most suitable for the administration route selected.

In one embodiment, Vaccine stabilizers used as part of the lyophilized vaccine, refer to chemical compounds added to vaccine formulations to enhance vaccine stability during periods of low temperature storage, lyophilization processing, or storage post-lyophilization. In one embodiment, the stabilizer aqueous solutions used for formulating and stabilizing the vaccine or mesothelioma tumor cells generated according to the methods described in the embodiments hereinabove used in the compositions or methods of the invention comprise a high molecular weigh structural additive, a disaccharide, a sugar, alcohol and water. In another embodiment, the aqueous solution also includes one or two amino acids and a buffering component. The combination of these components act in one embodiment to preserve the activity of vaccine or mesothelioma tumor cells generated according to the methods described in the embodiments hereinabove, upon freezing and lyophilization and a long storage period subsequent to lyophilization.

In one embodiment, the compositions described herein, which are used in the methods described herein further comprise a pharmaceutically acceptable carrier, excipient, flow agent, processing aid, diluent or a combination thereof.

In one embodiment, the vaccines and compositions described hereinabove, which are generated by the methods described herein, are used in the methods described herein.

In one embodiment, provided herein is a method of treating mesothelioma in a subject, comprising the step of administering to said subject a composition comprising a vaccine for the treatment of mesothelioma prepared by treating mesothelioma cells with a photosensitizer; removing the photosensitizer from the cells; incubating the photosensitized cells; and exposing the photosensitized cells to electromagnetic energy source; whereby the exposure of the photosensitized incubated cells to the electromagnetic radiation kills the cells, thereby resulting in non-viable cells capable of inducing immunological response.

In another embodiment, provided herein is a method of treating mesothelioma in a subject, comprising administering to said subject a composition for treating, preventing or ameliorating mesothelioma in a subject, comprising: a pharmaceutically acceptable carrier and an immunologically effective amount of a vaccine for the treatment of mesothelioma prepared by treating mesothelioma cells with a photosensitizer; removing the photosensitizer from the cells; incubating the photosensitized cells; and exposing the photosensitized cells to electromagnetic energy source; whereby the exposure of the photosensitized incubated cells to the electromagnetic radiation kills the cells, thereby resulting in non-viable cells capable of inducing immunological response.

In one embodiment, administering of the vaccines and compositions described in the embodiments hereinabove, is done intravenously, or intratumorally, intraaorterially, intramuscularly, subcutaneously, parenterally, transmucosally, transdermally, or topically. In another embodiment, the vaccine is in a lyophilized, an aerosolized, or a parenteral form.

In one embodiment, the invention provides a combination vaccine, comprising a vaccine for the treatment of mesothelioma prepared by treating mesothelioma cells with a photosensitizer; removing the photosensitizer from the cells; incubating the photosensitized cells; and exposing the photosensitized cells to electromagnetic energy source; whereby the exposure of the photosensitized incubated cells to the electromagnetic radiation kills the cells, thereby resulting in non-viable cells capable of inducing immunological response, together with one or more antigens that trigger an immune response that protects a subject against mesothelioma, and a pharmaceutically acceptable carrier. In another embodiment, the one or more antigens that trigger an immune response that protects a subject against mesothelioma is SV40, or IL-2, IL12, CD40$^+$, or a combination thereof in other embodiments.

The term "about" as used herein means in quantitative terms plus or minus 5%, or in another embodiment plus or minus 10%, or in another embodiment plus or minus 15%, or in another embodiment plus or minus 20%.

The term "subject" refers in one embodiment to a mammal including a human in need of therapy for, or susceptible to, a condition or its sequelae. The subject may include dogs, cats, pigs, cows, sheep, goats, horses, rats, and mice and humans. The term "subject" does not exclude an individual that is normal in all respects.

The following examples are presented in order to more fully illustrate the preferred embodiments of the invention. They should in no way be construed, however, as limiting the broad scope of the invention.

EXAMPLES

Materials and Methods

Cell Line

AB1, murine malignant pleural mesothelioma (MPM) was utilized for vaccine preparation and host tumor challenge. AB1 cell line was donated by Dr. Steven Albelda, from the Hospital of the University of Pennsylvania.

LKR13, a murine bronchioloalveolar carcinoma cell line provided by the Howard Hughes Medical Institution, was utilized for host tumor re-challenge for animals not previously vaccinated against this cell line. This cell line was derived from lung cancers that had spontaneously developed in transgenic mice following somatic activation of the k-ras oncogene, Animals BALB/c (AB1 tumor host) mice, obtained pathogen-free from the Jackson Laboratory (Bar Harbor, Me.) were used for all the experiments. Animals were housed in a barrier facility in microisolator cages in a laminar flow unit under ambient light. A murine mesothelioma cell line was used (AB1). BALB/c mice are an immunocompetent, nearly syngeneic, inbred strain of mice.

Additionally, six to twelve week old, female BALB/cJ (AB1 tumor host) mice, obtained pathogen-free from Taconic Farms, were used for certain experiments. All animal studies were performed following a protocol approved by the University of Pennsylvania Institutional Animal Care and Use Committee.

Animals were kept in conventional conditions in microisolator cages in laminar flow unit under ambient light with full access to food and water during experiments. Forty animals were administered weekly vaccinations of PDT, IR, F/T (freeze-thaw), or PBS (sham) for two weeks by way of subcutaneous injection. By day 21, all groups were challenged with intra-thoracic inoculation of $1\times10^5$ AB1 murine mesothelioma cells harvested from exponentially growing cultures. Animals were sacrificed when signs of distress (such as weight loss, ruffled fur, or loss of appetite) are exhibited and were correlated to visualized tumor burden at necropsy Tumor Growth Curves To establish tumor growth curves, animals were injected subcutaneously in their left flanks. Initial tumor growth curves were obtained from injections of $1\times10^6$ tumor cells harvested from exponentially growing cultures. Animals were monitored for 60 days or until tumor volume exceeded approximately 700 mm$^3$, whichever came first. At least 10 mice were used for each experimental group, in order to maintain statistical accuracy. This concentration of tumor cells led to overly rapid tumor growth, so the tumor growth curve was repeated under the same conditions, using injections of $5\times10^5$ cells.

Light Dose Determination

Initial tests were conducted in order to explore the possibility of generating inactivated whole tumor cells from PDT. Three variables were manipulated: Photofrin® incubation time, Photofrin® dosage, and light dosage. Since Photofrin® incubation times may determine cellular uptake—either just within the membrane or further into the cytoplasm—the cells were incubated for either 3-hours or 24-hours, followed by a 3-hour incubation in drug-free media. Second, cells were given a Photofrin dose of either 10 µg/mL or 25 µg/mL. Dosages were determined by consulting both past papers and another PDT research laboratory. Lastly, light dosage was varied. The light source was a Laserscope KTP/YAG laser with a 630 nm Dye Module. Cells were lit at 630 nm—red wavelength within the visible spectrum and the most effective wavelength for Photofrin®. Laser light dosage was measured in fluence or j/cm$^2$. Light dosages ranged from 0.125 j/cm$^2$ to 1.0 j/cm$^2$.

Later in the study, dose-response curves followed by clonogenic assays, were performed in order to determine appropriate PDT light dosages for complete cell killing. In these tests, cells were incubated for 24-hours and exposed to high light dosages ranging from 1.0 j/cm$^2$ to 3.0 j/cm$^2$. The clonogenic assay measured cell plating efficiency and proliferation and involved plating cells at very low concentrations. After one week, resultant colonies that had formed were counted and compared against controls that had not been lit.

Vaccine Preparation and Photodynamic Therapy

AB1 cells were grown in DMEM supplemented with 10% FBS (Fetal Bovine Serum) and gentamicin (all from Gibco). All cells were cultured in a humidified atmosphere of 5% CO$_2$ in air at 37° C. Three types of vaccines were used in this trial: freeze-thawed cells (F/T), irradiated cells (IR), and photodynamic therapy cells (PDT).

All vaccines were made from $1\times10^6$ AB1 cells treated with either F/T, IR, or PDT. Vaccines were delivered subcutaneously in 100 µl of serum-free media in the flank. F/T vaccine was made by freezing the cells in liquid nitrogen and then thawing them in three successive cycles. IR vaccine was created by exposing cells to 50 gray of radiation. PDT vaccine was created as follows. Exponentially growing cells were first treated with Photofrin® at a dose of 25 µg/mL and incubated for 3 or 24 hours. The Photofrin® was then removed, the media replaced, and cells incubated for an additional 2 hours. Cells were then placed in serum-free media and transferred to a plate in preparation for lighting. Our light source was a Laserscope KTP/YAG laser with a 630 nm Dye Module. Cells were lit at 630 nm—red wavelength within the visible spectrum and wavelength with the optimal combination of tissue penetration and effectiveness for Photofrin®. Laser light dosage was measured in fluence or $j/cm^2$.

All vaccines were administered sub-cutaneously in the flank with $1\times10^6$ treated cells. In our first round of PDT vaccine treatment, prepared cells were incubated for 3 hours with Photofrin® and treated with 2.0 $j/cm^2$ and the intention of complete cell kill. However, upon vaccine administration, mice developed tumors, indicating that not all cells had been killed. This result was unexpected because of the high light dosage.

For subsequent PDT vaccines, cells were incubated for 24-hours in Photofrin® and lit with 3.0 $j/cm^2$ to ensure cell death.

Tumor Challenge

Initial tumor challenges after vaccination were given as sub-cutaneous injections in the flank. $5\times10^5$ cells were injected. However, this method resulted in inconsistent growth and erratic tumor volumes, calling for another method of cell delivery.

Tumor challenges were performed using an innovative intra-thoracic (IT) model. Such a procedure is first of all, gave more consistent tumor growth between mice in a treatment group, and second of all, is more clinically relevant. Precedent IT injections were performed by the Korst lab (Merritt, R. E., Yamada, R. E., Wasif, N., Crystal, R. G., and Korst, R. J. Effect of inhibition of multiple steps of angiogenesis in syngeneic murine pleural mesothelioma. Ann Thorac Surg, 78: 1042-1051, 2004). With this method of delivery, mesothelioma cells were injected into the pleural space, generating a more consistent orthotopic model.

The initial trials of IT injections involved the following procedure: mice were first anesthetized with isofluorane and their skin prepped with betadine to clean the area. An incision on the side of the mouse was made through the skin and muscle layers until the rib cage was exposed and the lung could be visualized through the parietal pleura. A small incision was made in the pleura, which introduced air into the pleural space, causing the lung to collapse. A syringe was quickly inserted into this space and $5\times10^5$ cells were injected. A catheter was placed into the small incision and air was withdrawn from the pleural space, creating a negative pressure and reinflating the lungs. A suture was placed to close the space and maintain lung inflation and the remaining layers of tissue and skin from the initial incision were sutured and closed.

While this technique ensured that tumor cells were injected into the appropriate place and cells were not introduced into the lung itself, there was a relatively high rate of mortality from the procedure. Mice were significantly distressed when one lung was collapsed and sometimes could not survive the surgery.

The technique was amended and improved by switching to the "hook" method. All initial steps remained the same. The mouse was first anesthetized. A small incision was made in the skin and the tissue dissected down to the pleural layer. Cells were then directly injected into the pleural space via a bent or 'hooked' needle. The tissue layers and skin were then sutured. This method avoided making a small incision in the intercostal tissue and causing a pneumothorax. This method resulted in a higher survival rate. This IT injection led to orthotopic tumor growth in the pleural space without growth in the lung.

Vaccines were given three weeks before tumor challenge with a booster one week before challenge. A summary of the vaccine design and timetable is shown in Table 1.

TABLE I

Timeline and schedule of experiment design and setup for vaccine studies.

| Day | Control | PDT | F/T | IR |
|---|---|---|---|---|
| −3 weeks | PBS | 1E6 AB1, PDT | 1E6 AB1, F/T | 1E6 AB1, IR |
| −1 week | PBS | 1E6 AB1, PDT | 1E6 AB1, F/T | 1E6 AB1, IR |
| 0 | Injection, 5E5 AB1 | Injection, 5E5 AB1 | Injection, 5E5 AB1 | Injection, 5E5 AB1 |
| 30 days or until death | Thrice-weekly measurements for all groups | | | |

Tumor Growth Curves

Flank model growth curves showed erratic growth. Injections of $1\times10^6$ AB1 cells lead to overly rapid tumor formation, and injections of $5\times10^5$ AB1 cells lead to unpredictable growth. Therefore, the intra-thoracic mesothelioma model was proposed and used for later injections.

Light-Dose Determination (2)

Dose-response studies that varied Photofrin® concentrations, Photofrin® incubation times, and light dosages showed that obtaining purely inactivated but not dead cells was not possible. All three factors were modified with the intent of producing complete cell death. Cells were incubated in 25 µg/mL of Photofrin® for 3 hours and lit with 2.0 $j/cm^2$ of light at 630 nm. This regimen unexpectedly led to tumor growth from the vaccine injection. A clonogenic assay was performed to explore the dose-response relationship at this level of light, and the results are summarized in Table 2. For the assay, cells were incubated in 25 µg/mL of Photofrin® for 24 hours and lit with 1.0 to 3.0 $j/cm^2$ of light. Interestingly, the assay showed nearly complete cell kill in all conditions, with light dosages ranging from 1.0 to 3.0 $j/cm^2$. After this test, PDT vaccines were generated by incubating cells in 25 µg/mL of Photofrin® for 24 hours and lit with 3.0 $j/cm^2$ of light.

TABLE II

Results of the clonogenic assay

| Conc. | Control | 1.0 | 1.5 | 2.0 | 2.0 (100 mill) | 2.5 | 3.0 | 3.0 (100 mill) |
|---|---|---|---|---|---|---|---|---|
| | | | | Clonogenic Results | | | | |
| 250 | 44 | | 0 | | | | | |
| 250 | 53 | | 0 | | | | | |
| 250 | 63 | | 0 | | | | | |
| 500 | 79 | 0 | 0 | 0 | 0 | 0 | 0 | 0 |

TABLE II-continued

Results of the clonogenic assay

| Conc. | Control | 1.0 | 1.5 | 2.0 | 2.0 (100 mill) | 2.5 | 3.0 | 3.0 (100 mill) |
|---|---|---|---|---|---|---|---|---|
| 500 | 113 | 0 | 0 | 0 | 0 | 0 | 0 | 1 |
| 500 | 110 | 0 | 0 | 0 | 0 | 0 | 0 | 0 |
| 1000 | 208 | 0 | 0 | 0 | 0 | 0 | 0 | 0 |
| 1000 | 223 | 0 | 0 | 0 | 0 | 0 | 0 | 0 |
| 1000 | 230 | 1 | 0 | 1 | 0 | 0 | 0 | 2 |
| Averaged numbers: | | | | | | | | |
| 250 | 53.33 | | 0.00 | | | | | |
| 500 | 100.67 | 0.00 | 0.00 | 0.00 | 0 | 0 | 0 | 0.33 |
| 1000 | 220.33 | 0.33 | 0.00 | 0.33 | 0 | 0 | 0 | 0.67 |
| % Cell Kill | | | | | | | | |
| 250 | | | 100 | | | | | |
| 500 | | 100 | 100 | 100 | 100 | 100 | 100 | 99.67 |
| 1000 | | 99.85 | 100.00 | 99.85 | 100 | 100 | 100 | 99.70 |

Assay was performed at three concentrations of cells: 250, 500, and 1,000 cells per plate. Cells were treated with Photofrin ® for 24 hours and lit at five different light dosages: 1.0, 1.5, 2.0, 2.5, and 3.0 j/cm². Of the cells that were lit with 2.0 and 3.0 j/cm², some of the plates were lit at high concentrations of cells to see if cell density during lighting would effect cell proliferation. The results showed nearly total kill across all conditions Re-Challenge of PDT, IR, and F/T Vaccinated Mice Ninety days after initial intra-thoracic AB1 tumor challenge PDT, IR and F/T vaccinated groups were administered opposing bilateral flank injections of AB1 and LKR-13 cell lines at a concentration of $5 \times 10^6$ cells/100 μL. Mice were observed for thirty days or until palpable tumors were apparent ($\approx 250$ mm³) at which time the tumors were excised for identification and animals euthanized.

Generation of Lysates for Vaccination

AB1 murine mesothelioma cells were maintained in complete Dulbecco's Modified Eagle Medium (DMEM) supplemented with 10% fetal bovine serum (Sigma-Aldrich, St. Louis, Mo.), and 1% gentamicin (Invitrogen, Carlsbad, Calif.). All of the cells were cultured in a humidified atmosphere of 5% CO2 in air at 37° C. For PDT-generated lysates, exponentially cells were incubated with 10.0 μg/ml clinical-grade Photofrin® (Axcan Pharma Inc., QC, Canada) in phenol-free 5% FBS medium for 24 h. Cells were removed from culture flasks with trypsin-EDTA (Invitrogen), washed once with complete medium, and placed in Petri dishes to avoid attachment. They were then transferred to serum-free medium at $1 \times 10^7$ cells/ml and illuminated with 630 nm light via a 630 nm dye laser system (Laserscope, San Jose, Calif.) at a dose of approximately 1 J/cm². IR lysates were generated by treatment of the cells ($1 \times 10^7$ cell/ml) with 25 Gy of γ-irradiation. F/T lysates were generated by subjecting cells ($1 \times 10^7$ cell/ml) to three F/T cycles. The cycles required cells to be frozen in liquid nitrogen and then thawed at in a 50° C. waterbath. Total cell disruption was microscopically confirmed using trypan blue staining.

ELISPOT Assay for Interferon-γ (IFN-γ)

Vaccinated and control mice were sacrificed three days after the second vaccination. Spleens were harvested, RBC-depleted single cell suspensions were generated, and ELISPOT assays were used to quantitate the numbers of IFN-γ secreting cells. The capture antibody, a purified anti-mouse IFN-γ antibody (eBioscience, San Diego, Calif.), was diluted in sterile ELISPOT Coating Buffer (eBioscience). The ester cellulose-bottom plate (Millipore, Bedford, Miss.) was coated with 100 μl/well of the capture antibody solution and then incubated at 4° C. overnight. Spleen cells at $5 \times 10^6$ cells/ml culture medium (complete-RPMI 1640 supplemented with 10% FBS) were added to the plate (100 μl/well). The cells were incubated for 24 h at 37° C. with or without stimulation. For stimulation, either ConA (1 μg/ml; positive control), F/T, PDT, or IR-generated lysates in a total volume of 50 μl was added. After the culture period, cells were removed by washing the plate in PBS-Tween (0.05%), and 100 μl/well of biotinylated IFN-γ detection antibody (eBioscience) was then added. The plate was incubated at room temperature for 2 h. The antibody was then removed, and streptavidin-horseradish peroxidase (eBioscience) was added. The plate was incubated for 45 minutes. After incubation, 100 μl/well of freshly prepared substrate AEC (eBioscience) was added. Spots were developed with the substrate AEC. Each spot represents an IFN-γ-secreting cell. Each sample was plated in triplicate.

Western Blot Analysis for HSP-70 Expression

Control cells and each respective cell vaccine preparation were collected and lysed in 60 μL of lysis buffer (20 mM Tris, pH 7.6, 1% Triton-X 100, 2 mM EDTA, 10% glycerol, 1 mM DTT, 1 m Morthovanadate and 1× Complete Protease Cocktail tablet). After electrophoresis, the proteins were transferred onto a nitrocellulose membrane by electroblotting using 100 volts for 1 h. The membrane was then incubated in 5% dry milk blocking solution containing 1:5000 primary antibody (Mouse Monoclonal IgG1, Affinity BioReagents, Golden, Colo.) for 1 h. The membrane was washed and incubated with 5% dry milk blocking solution containing 1:2500 secondary antibody (HRP conjugate antibody, Affinity BioReagents) for 1 h. After washing with 1×PBS, the membrane was then stained by using ECL detection kit (Amersham, Chalfont, UK).

Statistical Analysis

A Fisher's Exact test was performed in order to statistically analyze the results. The test yielded a $p=0.033$, indicating that this results were significant.

Example 1

PDT Treated Vaccine is Effective in Mesothelioma Tumor Suppression

Preliminary Vaccine Trial

Figure 2:
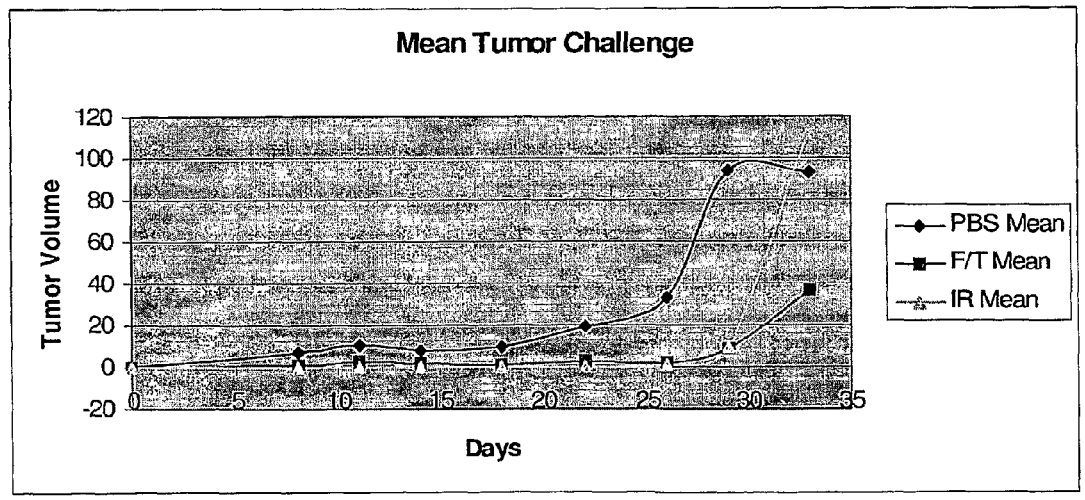
FIG. 2 shows plot of mean tumor volumes in three treatment groups: control (PBS), F/T, and IR.
Figure 3:
FIG. 3 shows non-vaccinated mouse thorax, showing large tumor masses throughout the pleural space (arrows)

Mice were vaccinated with $1 \times 10^6$ treated cells in the flank and tumor challenged in the flank. Because the PDT group vaccine grew tumor, the mice were sacrificed, and data is only available for the remaining three groups: control, F/T, and IR. Each group contained 10 mice. Unpredictable growth after tumor challenges made the data difficult to interpret, as some mice grew tumors quickly and others grew no tumor. FIG. 1 shows a scatter plot of the collected tumor volumes, demonstrating the spread and inconsistency of the data. FIG. 2 shows a plot of the average tumor volumes of all three groups. The PBS (control) group shows a downward fall at the end because the average was skewed when the mouse with the largest tumor was euthanized Second Vaccine Trial This vaccine trial involved vaccinations in the flank and IT injected tumor challenges. In this trial, only two treatment groups were defined: a PDT vaccine and a control group. Each group originally contained 10 mice. However, two mice died during injections in the PDT group, and in the control group, three mice died during the surgery. Vaccine effectiveness was measured as a function of survival, with mice euthanized when they began showing classic signs of discomfort, such as weight loss, ruffled fur, and labored breathing. In the control group, 7 of the 9 mice were sacrificed because of tumor growth. 2 of 9 mice had no discernible tumor. All 7 mice were examined after death for evidence of gross tumor. 6 of the 7 mice showed significant tumor growth (FIG. 3). One mouse showed tumor nodules within its entire abdominal cavity, which we believe to be a result of an injection that was below the diaphragm and had entered the abdomen rather than the pleural space.

Figure 4:
FIG. 4 shows PDT-vaccinated mouse thorax with inflated lungs.
Figure 5:
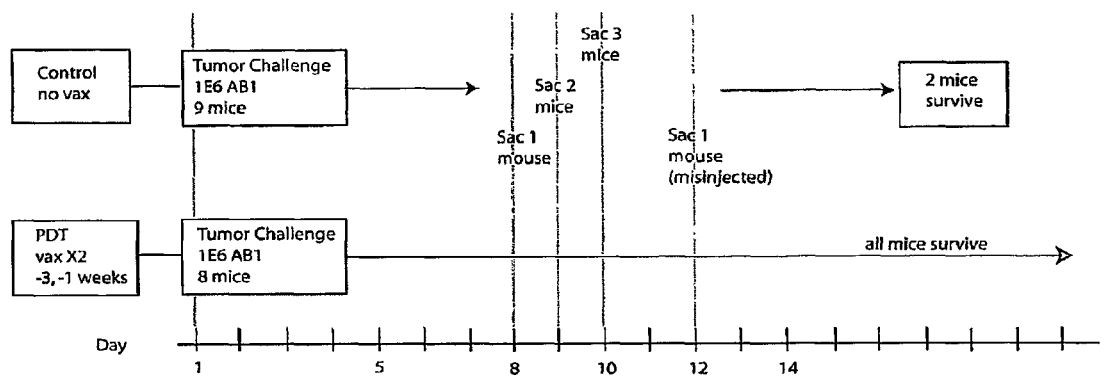
FIG. 5 shows summary of experiment results of two treatments: control (no vax) and PDT vaccine groups.
Figure 6:
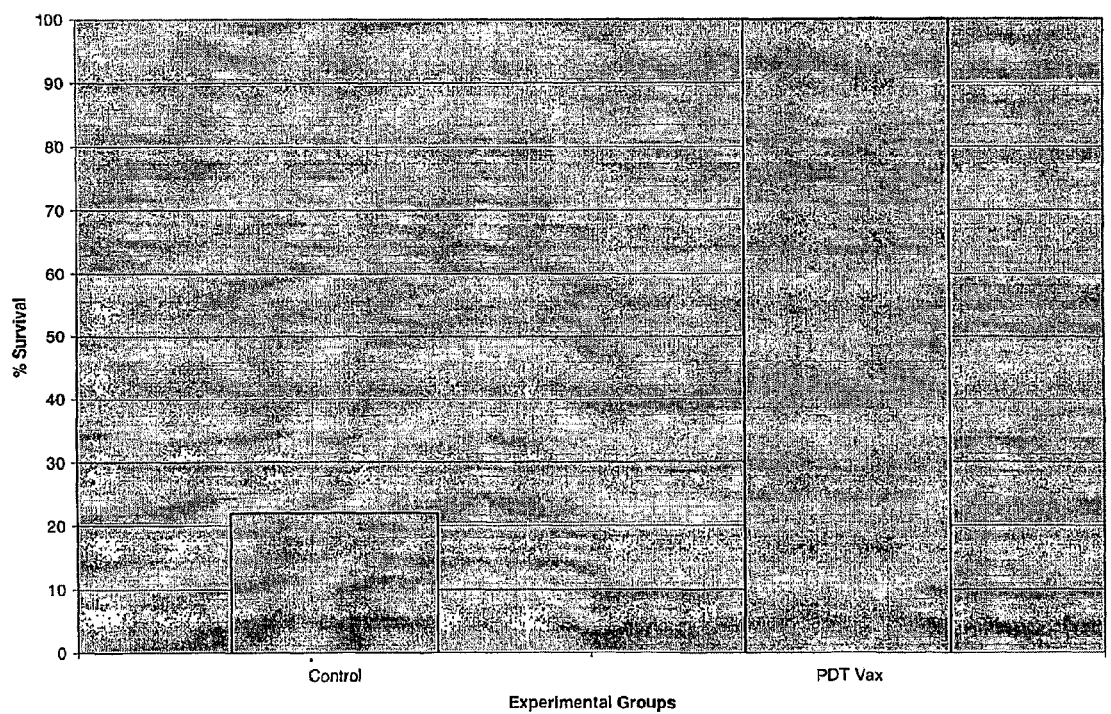
FIG. 6 shows the preliminary results for PDT-generated vaccine.

The 6 mice that presented with significant tumor growth in the chest cavity died within two days, showing good consistency. The mouse with tumor in its abdomen proved that tumor would at least grow, which was a positive result. And the two mice that did not grow tumor remain inconclusive, most probably due to technical error during tumor inoculation. Upon gross examination of sacrificed mice with tumor growth in the chest, tumors grew well in the pleural space and did not seem to invade into the lungs, showing that the IT technique was successful In the PDT group, there was no tumor growth in any of the mice. They were followed for a mean of 53 days. After this period of time, they were sacrificed and examined; 8/8 (100%) showed no evidence of gross tumor mass (FIG. 4). All were healthy until time of sacrifice. The design and results of this portion of the experiment are summarized in FIG. 5.

Summary

A broad summary of the different portions of the experiment is in Table III.

TABLE III

Summary of Experiment

Flank Injections
Tumor Growth Curve Determination

| | # cells | Results |
|---|---|---|
| Tumor Growth | 1E6 AB1 | Tumor growth too rapid |
| Tumor Growth | 5E5 AB1 | Inconsistent growth |

| Treatment | | Tumor Challenge | Results |
|---|---|---|---|
| Vaccine Studies: Vaccinated with 1E6 treated cells; −4, −1 weeks | | | |
| Control | PBS | 5E5 AB1 | Inconsistent growth |
| PDT | PDT, 2.0 j/cm² | n/a | Vaccine led to tumor growth |
| F/T | F/T | 5E5 AB1 | Inconsistent growth |
| IR | IR | 5E5 AB1 | 1/10 grew tumor |
| | | IT Injections | |
| Vaccine Studies: Vaccinated with 1E6 treated cells; −3, −1 weeks | | | |
| Control | PBS | 5E5 AB1 | 7/9 grew tumor |
| PDT | PDT, 3.0 j/cm² | 5E5 AB1 | 0/8 grew tumor |

Example 2

Figure 7:
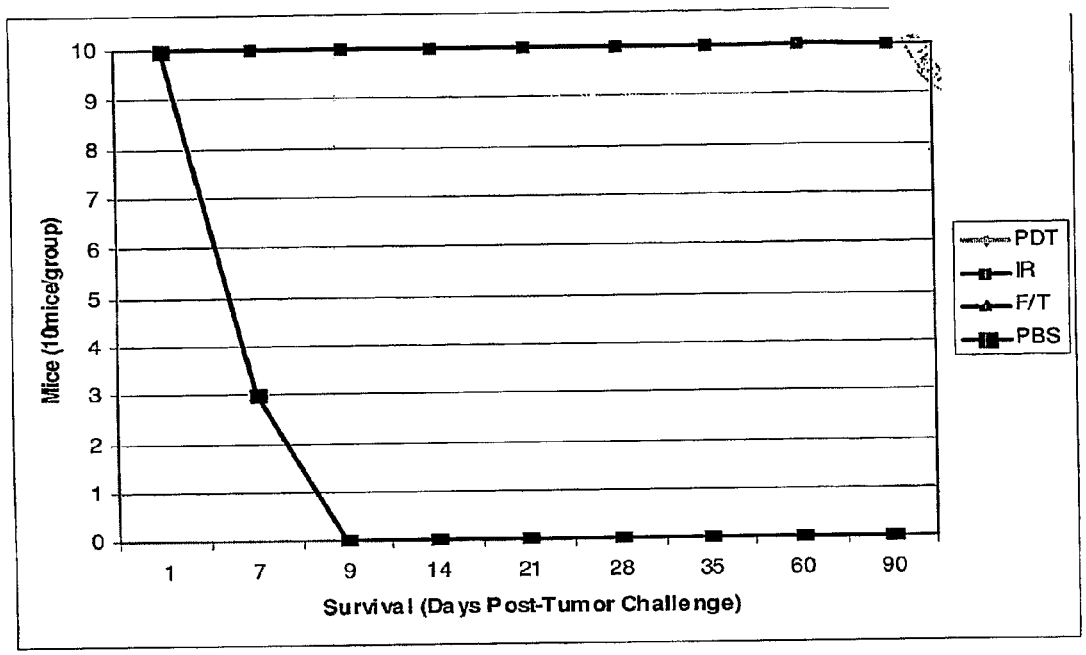
FIG. 7 shows how by day 9 all PBS vaccinated mice died secondary to tumor burden. IR, F/T, and PDT continued to survive the entire ninety days of the study.

PDT Generated Lysates Enhance Cellular Immunogenicity and Host Tumor Specific Immunity To further elucidate the immunogenic role of PDT in the treatment of malignant mesothelioma the capability of in vitro PDT generated lysates to impel a tumor-specific cytotoxic response from the host immunity was tested. Naive mice were vaccinated with the previously described preparations of PDT, IR, F/T or media alone and subsequently challenged with expotentially growing tumor cells via intra-thoracic inoculation. By day 7, seven of ten of the sham vaccinated mice had expired secondary to tumor burden. By day 10 all mice given sham vaccinations died secondary to tumor burden. FIG. 3 shows a PBS vaccinated mouse that died at day 9 secondary to tumor burden and shown in FIG. 4, is a PDT-vaccinated mouse sacrificed at day 90 for visual inspection of pleural cavity which is clearly free of any disease. All mice in groups receiving PDT, F/T, and IR vaccinations continued to survive with no deaths in any group ninety days post intra-thoracic tumor challenge. FIG. 7 demonstrates the prophylactic immunity provided to the groups vaccinated with PDT, F/T, and IR. Groups receiving autologous tumor vaccination of any preparation exhibited significant immunity upon intra-thoracic tumor challenge when compared to animals administered a sham vaccine.

All surviving PDT, F/T, and IR animals were subsequently re-challenged with both AB1 and LKR13 cells on opposing flanks. The PDT vaccinated mice presented with no palpable AB1 cell line 30 days post re-challenge but possessed a large LKR-13 tumor. Ten days after re-challenge all mice in each group had actively growing LKR-13 tumors on the right flank but only the IR and F/T vaccinated mice exhibited tumor growth of the AB1 cell line on the left flank. By day 30 all mice were euthanized as their respective tumors reached endpoint but only the PDT vaccinated animals exhibited tumor specific immunity.

Example 3

PDT Vaccines Heighten Splenocyte IFN-γ Secretion and HSP-70 Expression

Figure 9:
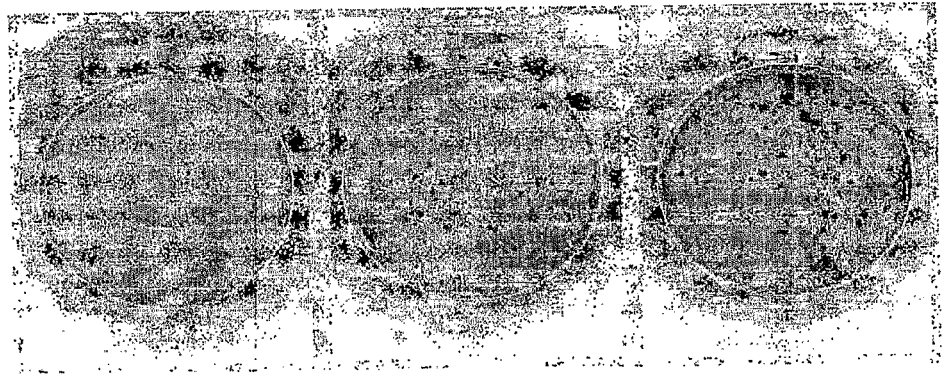
FIG. 9 shows ELISPOT IFN-γ Assay. Splenocytes harvested from A—Freeze/Thaw, B—IR, and C—PDT vaccinated mice and quantified for IFN-γ secreting cells. PDT-generated lysates exhibited highest levels of splenocyte activation

Splenocyte activation for each vaccine preparation was examined by ELISPOT analysis. Spleens harvested from vaccinated mice and assayed for IFN-γ secretion showed significantly higher levels of IFN-γ when stimulated by PDT generated cell lysates compared with splenocytes from animals vaccinated with media alone. Stimulated splenocytes collected from PDT vaccinated mice also possessed significantly higher IFN-γ secretion in comparison with stimulated splenocytes collected from IR or F/T vaccinated animals as seen in FIG. 9. There also appeared to be a slight increase in IFN-γ secretion in the IR vaccinated animals compared to the F/T vaccinations.

Figure 8:
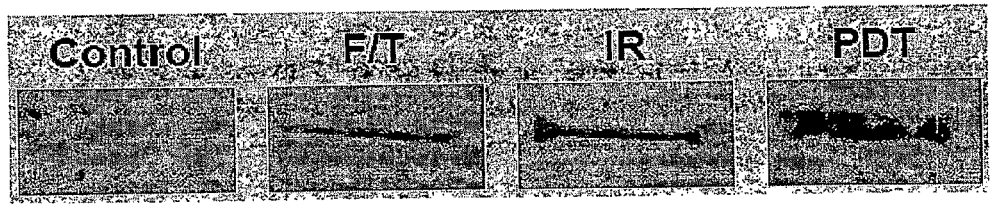
FIG. 8 shows. Western Blot Analysis for Heat Shock Protein-70. Results show highest HSP-70 protein expression in PDT-derived vaccine compared to F/T and IR.

The stress conditions experienced by the cells for each vaccine were examined by measuring HSP-70 protein expression by Western Blot analysis. HSP-70 has been linked as a potential mediator for stimulation of host immune response. Protein was recovered from each vaccine preparation (PDT, IR, F/T) and control cells and assayed for expression of HSP-70. PDT-generated cell lysates exhibited significantly higher HSP-70 expression (FIG. 8) when compared to IR and F/T or control lysates which showed very little if no expression of HSP-70. The greater HSP-70 expression in PDT-generated lysates correlates with the notion that HSP-70 expression can induce dendritic cell activation and act as an antigen presenter in turn providing an immunologic advantage over vaccines prepared via F/T or IR methods.

12lijrh

Having described preferred embodiments of the invention with reference to the accompanying drawings, it is to be understood that the invention is not limited to the precise embodiments, and that various changes and modifications may be effected therein by those skilled in the art without departing from the scope or spirit of the invention as defined in the appended claims.

What is claimed is:

1. A method of preparing an autologous vaccine for the treatment of malignant mesothelioma in a subject, comprising the steps of: treating mesothelioma cells derived from said subject with a photosensitizer; removing the photosensitizer from the cells; and exposing the photosensitized cells to an electromagnetic radiation source; whereby the exposure of the photosensitized incubated cells to the electromagnetic radiation kills the cells.

2. The method of claim 1, wherein the photosensitizer is hematoporphyrin derivative (HPD), benzoporphyrin derivative (BPD), tetra(m-hydroxyphenyl)chlorin (foscan), mono-L-aspartylchlorin e6, lutetium texaphyrin, zinc phthalocyanine, or a combination thereof.

3. The method of claim 2, wherein the photosensitizer is hematoporphyrin derivative.

4. The method of claim 1, wherein said step of treating the exponentially growing mesothelioma cells with the photosensitizer is followed by incubation of the photosensitizer-treated cells for between about 3 to about 24 hours.

5. The method of claim 1, wherein the mesothelioma cells are exponentially growing malignant mesothelioma cells that do not produce TGF-$\beta$.

6. The method of claim 1, wherein said step of exposing, is preceded by placing the photosensitized cells in serum-free media and transferring them to a plate in preparation for exposure.

7. The method of claim 1, wherein the electromagnetic radiation source is laser light source.

8. The method of claim 1, wherein the electromagnetic radiation source is a light at a wavelength of 400-1200 nm.

9. The method of claim 8, wherein the lighting is at a wavelength of 630 nm.

10. The method of claim 1, wherein the mesothelioma cells treated are at the exponential growth phase.

11. A vaccine for the treatment of mesothelioma prepared by the method of claim 1, thereby resulting in non-viable cells capable of inducing immunological response.

12. A method of treating mesothelioma in a subject, comprising the step of administering to said subject the vaccine of claim 11.

13. A combination vaccine, comprising the vaccine of claim 11, together with one or more immunostimulating molecules that trigger an immune response that protects a subject against mesothelioma, and a pharmaceutically acceptable carrier.

14. The combination vaccine of claim 13, wherein the one or more immunostimulating molecules that trigger an immune response that protects a subject against mesothelioma is SV40, IL-2, IL12, CD40$^+$, HSP-70, IFN-$\gamma$, or a combination thereof.

15. A composition for treating, preventing the further progress of, delaying recurrence of, or ameliorating mesothelioma in a subject, comprising: a pharmaceutically acceptable carrier and an immunologically effective amount of the vaccine of claim 11.

16. The composition of claim 15, further comprising an adjuvant, cytokines, or their combination.

17. The composition of claim 16, wherein the adjuvant is an oil-in-water emulsion.

18. The composition of claim 15, wherein said composition is in a form suitable for oral, intravenous, intratumoral, intraaorterial, intramuscular, subcutaneous, parenteral, transmucosal, transdermal, or topical administration.

19. The composition of claim 15, further comprising an excipient, flow agent, processing aid, diluent or a combination thereof.

20. The composition of claim 15, in a liquid form.

21. A method of treating mesothelioma in a subject, comprising administering to said subject the composition of claim 15.

22. The method of claim 21, wherein said administering is intravenously, intratumorally, intraaorterially, intramuscularly, subcutaneously, parenterally, transmucosally, transdermally, or topically.

23. The composition of claim 15, wherein the vaccine is in a lyophilized, an aerosolized, or a parenteral form.

24. A method of preparing a vaccine for the treatment of malignant mesothelioma comprising the steps of: treating mesothelioma cells with a photosensitizer; removing the photosensitizer from the cells; and exposing the photosensitized cells to an electromagnetic radiation source; whereby the exposure of the photosensitized incubated cells to the electromagnetic radiation kills the cells, wherein the mesothelioma cells treated are at the exponential growth phase, and wherein the photosensitizer is present at a dose of between about 20 to about 30 $\mu$g/mL.

25. A method of preparing a vaccine for the treatment of malignant mesothelioma comprising the steps of: treating mesothelioma cells with a photosensitizer; removing the photosensitizer from the cells; and exposing the photosensitized cells to an electromagnetic radiation source; whereby the exposure of the photosensitized incubated cells to the electromagnetic radiation kills the cells, wherein the mesothelioma cells treated are at the exponential growth phase, and wherein the electromagnetic radiation dosage is above about 2.5 j/cm$^2$.

26. A method of increasing antigenicity of autologous malignant mesothelioma cells derived from a subject, comprising the steps of treating the mesothelioma cells with a photosensitizer; removing the photosensitizer from the cells; incubating the photosensitized cells; contacting the photosensitized cells with electromagnetic energy source; whereby the exposure of the photosensitized incubated cells to the electromagnetic radiation evokes IFN-$\gamma$ secretion, induces increased expression of HSP-70, or their combination, thereby increasing the antigenicity of the mesothelioma cells.

27. The method of claim 26, wherein the mesothelioma cells are isolated for treatment at the exponential growth phase.

28. A method of preparing an autologous vaccine for the treatment of malignant mesothelioma in a subject, comprising the steps of: treating mesothelioma cells derived from said subject with a photosensitizer; removing the photosensitizer from the cells; and exposing the photosensitized cells to an electromagnetic radiation source; whereby the exposure of the photosensitized incubated cells to the electromagnetic radiation kills the cells, and wherein the photosensitizer is present at a dose of between about 20 to about 30 $\mu$g/mL.

29. The method of claim 28, wherein the mesothelioma cells treated are at the exponential growth phase.

30. A method of preparing an autologous vaccine for the treatment of malignant mesothelioma in a subject, comprising the steps of: treating mesothelioma cells derived from said subject with a photosensitizer; removing the photosensitizer from the cells; and exposing the photosensitized cells to an electromagnetic radiation source; whereby the exposure of the photosensitized incubated cells to the electromagnetic radiation kills the cells, and wherein the electromagnetic radiation dosage is above about 2.5 j/cm$^2$.

31. The method of claim 30, wherein the mesothelioma cells treated are at the exponential growth phase.

* * * * *